United States Patent [19]

Nelson et al.

[11] Patent Number: 5,948,390

[45] Date of Patent: Sep. 7, 1999

[54] STABLE ZINC/CITRATE/CPC ORAL RINSE FORMULATIONS

[75] Inventors: Dennis G. A. Nelson, Mountain Lakes; Alenjandro V. Ortega, II, Jersey City, both of N.J.

[73] Assignee: Pfizer Inc., New York, N.Y.

[21] Appl. No.: 09/135,948

[22] Filed: Aug. 18, 1998

Related U.S. Application Data

[60] Provisional application No. 60/056,766, Aug. 25, 1997.

[51] Int. Cl.⁶ .............................. A61K 7/16; A61K 7/18; A61K 7/22; A61K 33/90
[52] U.S. Cl. .............................. 424/54; 424/49; 424/52; 424/641; 424/642
[58] Field of Search .............................. 424/49–58, 641, 424/642

[56] References Cited

U.S. PATENT DOCUMENTS

| | | | |
|---|---|---|---|
| 3,647,869 | 3/1972 | Kaloff | 260/535 P |
| 3,887,704 | 6/1975 | Lichtenstein | 424/145 |
| 4,011,309 | 3/1977 | Lutz | 424/49 |
| 4,022,880 | 5/1977 | Vinson et al. | 424/49 |
| 4,160,821 | 7/1979 | Sipos | 424/49 |
| 4,183,916 | 1/1980 | Rodon | 424/54 |
| 4,188,372 | 2/1980 | Gaffar | 424/54 |
| 4,273,759 | 6/1981 | Gaffar | 424/54 |
| 4,289,754 | 9/1981 | Dhabaar | 424/52 |
| 4,289,755 | 9/1981 | Dhabaar | 424/52 |
| 4,323,552 | 4/1982 | Schmolka | 424/54 |
| 4,325,939 | 4/1982 | Shah | 424/55 |
| 4,339,432 | 7/1982 | Ritchey et al. | 424/54 |
| 4,472,373 | 9/1984 | Ryan | 424/54 |
| 4,522,806 | 6/1985 | Muhlemann et al. | 424/52 |
| 4,545,979 | 10/1985 | Ambike et al. | 424/52 |
| 4,550,018 | 10/1985 | Ambike et al. | 424/52 |
| 4,606,912 | 8/1986 | Rudy et al. | 424/52 |
| 4,614,649 | 9/1986 | Gorman et al. | 424/54 |
| 4,689,214 | 8/1987 | Niles et al. | 424/49 |
| 4,986,981 | 1/1991 | Glace et al. | 424/50 |
| 4,994,262 | 2/1991 | Charbonneau et al. | 424/52 |
| 5,043,154 | 8/1991 | Gaffar | 424/52 |
| 5,100,650 | 3/1992 | Carlin et al. | 424/52 |
| 5,104,644 | 4/1992 | Douglas | 424/53 |
| 5,158,763 | 10/1992 | Gaffar | 424/54 |
| 5,174,990 | 12/1992 | Douglas | 424/53 |
| 5,176,901 | 1/1993 | Gallopo et al. | 424/54 |
| 5,178,869 | 1/1993 | Ebine et al. | 424/49 |
| 5,185,153 | 2/1993 | Pollock | 424/440 |
| 5,236,699 | 8/1993 | Libin | 424/54 |
| 5,266,306 | 11/1993 | Ohtsuki et al. | 424/54 |
| 5,292,527 | 3/1994 | Konopa | 424/54 |
| 5,294,432 | 3/1994 | Winston et al. | 424/52 |
| 5,300,289 | 4/1994 | Garlich et al. | 424/54 |
| 5,310,546 | 5/1994 | Douglas | 424/53 |
| 5,320,829 | 6/1994 | Garlich et al. | 424/54 |
| 5,320,830 | 6/1994 | Lukacovic et al. | 424/52 |
| 5,320,831 | 6/1994 | Majeti et al. | 424/52 |
| 5,330,748 | 7/1994 | Winston et al. | 424/49 |
| 5,372,802 | 12/1994 | Barrows et al. | 424/52 |
| 5,431,903 | 7/1995 | Majeti et al. | 424/52 |
| 5,437,856 | 8/1995 | Lukacovic et al. | 424/50 |
| 5,447,930 | 9/1995 | Nayak | 514/239.2 |
| 5,455,024 | 10/1995 | Winston et al. | 424/52 |
| 5,616,313 | 4/1997 | Williams et al. | 424/49 |
| 5,695,745 | 12/1997 | Barton et al. | 424/49 |
| 5,851,578 | 12/1998 | Gandhi | 426/590 |
| 5,855,873 | 1/1999 | Yam | 424/49 |

*Primary Examiner*—Shep K. Rose
*Attorney, Agent, or Firm*—Peter C. Richardson; Paul H. Ginsburg; Grover F. Fuller, Jr.

[57] ABSTRACT

A stable oral rinse or clear oral gel composition, comprising:
- a) about 0.01% by weight to about 1% by weight of hydrated zinc cations;
- b) about 0.01% by weight to about 4% by weight of fully or partially protonated citrate moieties;
- c) about 0.01% by weight to about 2% by weight of cetyl pyridinium cations; and
- d) an orally acceptable vehicle;

wherein said composition has a pH of from about 3.0 to about 4.5.

33 Claims, No Drawings

STABLE ZINC/CITRATE/CPC ORAL RINSE FORMULATIONS

This non-provisional application is based upon and claims priority from Provisional Application Ser. No. 60/056,766 filed Aug. 25, 1997.

The present invention relates to oral care products comprising zinc, citrate and cetyl pyridinium chloride (CPC).

BACKGROUND OF THE INVENTION

Most cases of oral malodor originate in the oral cavity and not from the stomach. Within the oral cavity, an important source of malodor is along the gumline, particularly in the approximal regions between teeth and in periodontal pockets. These are sites where bacteria accumulate into plaques and biofilms. Bacteria ferment and metabolize food debris at these sites to generate volatile sulfur compounds (VSCs), thought to be the main component of oral malodor. The main VSCs found in human oral malodor include hydrogen sulfide, methyl mercaptan and dimethyl sulfide although other mercaptans (R-SH) and sulfides ($R_2S$) are found in oral malodor. Another important source of malodor is the surface of the tongue which at the microscopic level contains many recessed folds and cavities in which micro-organisms grow and flourish. Again, these are good sites for the production of VSCs. Impaired or reduced salivary flow also seems to correlate with increased oral malodor. Since oral micro-organisms are responsible for the VSCs originating in the oral cavity, the chronic use of antimicrobials in oral compositions has been found to improve oral malodor. Also, oral compositions containing zinc salts have been used to treat VSCs because they strongly complex with these sulfur compounds, thus rendering them non-volatile and no longer able to cause malodor.

Zinc salts have been used in oral compositions because they possess both antimicrobial and oral deodorizing properties when appropriately formulated. In particular, for zinc salts to be effective in an oral composition, they should be solubilized in a form that is either uncomplexed or weakly-complexed. Unfortunately, uncomplexed or weakly-complexed zinc has an unpleasant, astringent taste as well as a drying, sometimes metallic, aftertaste. Thus, high levels of uncomplexed (or weakly-complexed) zinc, though effective, result in compositions that can be too astringent to be generally accepted by consumers. Zinc chloride, for example, has been used in compositions as the source of zinc ions. However, in order for these solutions or rinse compositions to be stable, they are formulated at acidic pHs of approximately 3.0 or less. These compositions, as mentioned above, also, have an astringent taste and an unacceptable aftertaste.

Several methods have been used to ameliorate the negative aesthetics of oral zinc compositions. One method, suitable only for dentifrices or solid dosage forms, involves using insoluble or sparingly soluble zinc salts such as zinc citrate. These salts then dissolve in saliva when they are introduced into the oral cavity, thus supplying the requisite zinc ions needed for efficacy. A second method is to complex the zinc ion with a chelating ligand so that the level of uncomplexed zinc is reduced. A third method, again, only suitable for dentifrices or solid dosage forms, is to physically encapsulate zinc salts with hydrophobic polymers. The use of such polymers, thus, provides a delivery system which results in the extended release of zinc.

In order to produce stable mouthwashes, oral rinses or gels that are optically clear, the first and third methods cannot be used. As a result, chelants have been used to solubilize insoluble zinc salts or to form clear, stable solutions or gels above pH=3.0 (U.S. Pat. Nos. 4,289,754; 4,289,755; and 4,325,939, insoluble zinc citrate solubilized by excess citric acid and addition of sodium hydroxide to generate clear solutions with a pH of from 6.0 to 7.2).

Oral compositions have also been formulated with both zinc salts and CPC. U.S. Pat. Nos. 4,022,880 and 4,339,432 refer to the use of N-cetyl pyridinium chloride monohydrate (CPC) and zinc salts.

SUMMARY OF THE INVENTION

A stable oral rinse or clear oral gel composition, comprising:

a) about 0.01% by weight to about 1% by weight of zinc cations;

b) about 0.01% by weight to about 4% by weight of fully or partially protonated citrate moieties ( produced by adding citric acid, soluble citrate salts (e.g., sodium citrate, ammonium citrate, or potassium citrate), or mixtures thereof);

c) about 0.01% by weight to about 2% by weight of cetyl pyridinium cations; and d) an orally acceptable vehicle;

wherein said composition has a pH of from about 3.0 to about 4.5.

Zinc cations are preferably formed from zinc salts including zinc chloride, zinc sulfate, zinc gluconate, zinc acetate and zinc lactate.

The preferred cetyl pyridinium pharmaceutically acceptable salt is cetyl pyridinium chloride;

The combination of an antimicrobial such as CPC and a zinc salt should result in oral compositions which act to reduce oral malodor by using two different mechanisms of action. Such oral compositions are more advantageous than compositions that use only one mechanism of action.

DETAILED DESCRIPTION OF THE INVENTION

The dental formulations in this invention comprise stable oral rinse solutions and clear oral gels (e.g. gel dentifrice compositions) containing both hydrated zinc cations, fully or partially protonated citrate moieties and CPC in concentrations which provide effective antimicrobial and oral deodorizing properties while masking the unpleasant taste and aftertaste of zinc and CPC. The claimed invention results in stable, aesthetically acceptable zinc compositions where the zinc is not complexed and the pH lies in the range of from about 3.0 to about 4.5.

A suitable agent which does not strongly complex zinc in this pH range is citrate. The pKs of citric acid are 3.1, 4.8, and 6.4. Thus, the majority of citrate moieties at a pH range of between about 3.0 and about 4.5 are fully protonated $HO_2CCH_2C(OH)(CO_2H)CH_2CO_2H$ ($H_3CIT$) or partially protonated form ($H_2CIT^{1-}$, for example, $HO_2CCH_2C(OH)(CO_2H)CH_2CO_2^-$ or $HCIT^{2-}$, for example, $HO_2CCH_2C(OH)(CO_2^-)CH_2CO_2^-$). Complexation of citrate with zinc requires the presence of a triply ionized citrate anion ($CIT^{3-}$, for example, $^-O_2CCH_2C(OH)(CO_2^-)CH_2CO_2^-$), which does not occur appreciably at pHs below about 6. Complex species that can form between zinc and a triply ionized citrate anion under the appropriate conditions include $Zn(CIT)^-$, $Zn(CIT)_2^{4-}$ and $Zn(CIT)OH^{2-}$. The claimed zinc citrate compositions formulated in the above pH range of from about 3.0 to about 4.5 do not contain any appreciable amounts of these complex species and are stable with respect to low temperature cycling, defined by the permanent absence from flocculated material, precipitation or crystallization after low temperature storage at 7 days at −5° C. and subsequent return to room temperatures (25° C.).

Zinc cations, which include hydrated zinc cations, useful in the present invention are formed from soluble zinc salts (defined as at least 1 gm of material dissolved per 100 mls of water at 25° C.) that do not strongly complex zinc cations (defined as a log K (stability constant) less than 5) would be useful in the invention. Examples of such salts include zinc chloride, zinc sulfate, zinc gluconate, zinc acetate and zinc lactate. Examples of zinc salts that are not useful include zinc oxide and zinc citrate since they are not sufficiently soluble and will not dissolve in the pH range defined in this invention. Zinc cations are present in an amount ranging from about 0.01% by weight to about 1% by weight, preferably from about 0.02% by weight to about 0.25% by weight.

Various cetyl pyridinium pharmaceutically salts that are useful in the invention include N-cetyl pyridinium chloride monohydrate (available from EM Industries, Inc.) and cetyl pyridinium bromide. The preferred salt is include N-cetyl pyridinium chloride monohydrate (CPC). Cetyl pyridinium cations are present in an amount ranging from about 0.01% by weight to about 2% by weight, preferably from about 0.025% by weight to about 1% by weight.

The fully or partially protonated citrate moieties of the claimed compositions can be added as citric acid or various citrate pharmaceutically acceptable soluble salts, such as, for example, sodium citrate, ammonium citrate, potassium citrate, or mixtures thereof. The citrates are preferably used are sodium citrate, citric acid, or mixtures thereof. Soluble citrate salts are defined as at least 10 g of material dissolved per 100 ml of water at 25° C. Fully or partially protonated citrate moieties are present in an amount ranging from about 0.01% by weight to about 4% by weight, preferably from about 0.02% by weight to about 1% by weight.

Humectants are also useful in the oral composition of the present invention. They impart a moist and elegant feel to the mouth and if incorporated at sufficient concentration further inhibit the harshness of the phenolics in these compositions. Some humectants can also provide sweetness to the composition. Suitable humectants include edible polyhydric alcohols such as glycerin, sorbitol, propylene glycol, butylene glycol, xylitol and cyclodextrins including its derivatives. The humectant generally is present in an amount ranging from about 0.1% by weight to about 30% by weight for oral rinses and from about 10% by weight to about 50% by weight for oral gel compositions.

Oral surfactants are also useful in the present invention, however, those that are useful in the present invention should be compatible with CPC and, thus, include certain nonionic and amphoteric surfactants. The preferred oral surfactants include block co-polymers of polyoxyethylene and polyoxypropylene such as the Pluronics from BASF. Other nonionic surfactants that are useful include polysorbate surfactants such as the Tweens from ICI. Amphoteric surfactants that can be used include betaines, sulfobetaines and amidobetaines such as the TEGO betaines from Goldschmidt Chemical Corporation. Mixtures of nonionic and amphoteric surfactants can also be used. These surfactants are generally present in amounts of from about 0.01% by weight to about 10% by weight, most preferably from about 0.01% by weight to 1% by weight for oral rinses and from about 0.5% by weight to about 5% by weight for oral gels.

The liquid carrier of the invention generally includes mixtures of water and ethanol for oral rinses, although the carrier can be alcohol-free, especially in oral gels. For oral rinses, the amount of water ranges from about 50% by weight to about 85% by weight. The amount of alcohol for oral rinses ranges from about 0% by weight to about 25% by weight, preferably from about 0% by weight to about 15% by weight. For oral gels, the amount of water ranges from about 0% by weight to about 60% by weight, preferably from about 0% by weight to about 40% by weight.

The oral rinse and oral gel compositions are stable so as to be substantially optically clear and substantially free of precipitation, flocculation, or crystal formation at about room temperature (about 25° C.) as well as at low temperatures of at least about 5° C. for at least about 1 week. The low temperature stability of these compositions is determined by cooling the compositions to about 5° C., storing for at least seven days and determining whether any precipitate, crystallized or flocculated material is formed in the clear compositions (solutions and gels).

For gel compositions, abrasives may also be added. Suitable abrasives include precipitated silica or silica gels which have an average particle size ranging from about 0.1 to about 50 microns which are treated so as to be compatible with cationic zinc and cationic CPC. Compatible abrasives should not substantially inactivate the zinc and CPC in the composition. Preferred silica abrasives include those marketed under the tradename "Sylodent" or "Syloid" by the W. R. Grace & Co. and those marketed under the tradename "Zeodent" by the J. M. Huber Corp. Other suitable abrasives, having a suitable particle size as described above, include β-phase calcium pyrophosphate, alumina and calcium carbonate. The amount of abrasive in a gel composition ranges up to about 60% by weight, preferably from about 10% by weight to about 40% by weight.

Oral rinse and gel compositions of the present invention may also contain a suitable fluoride source. Typical sources include soluble salts of the fluoride ion (e.g. sodium fluoride, potassium fluoride, stannous fluoride, stannous fluorozirconate) or, soluble salts of the monofluorophosphate ion (e.g. sodium monofluorophosphate). The preferred fluoride source is sodium fluoride. The fluoride ion source should provide from about 50 ppm to about 2500 ppm fluoride, preferably from about 250 ppm to about 1500 ppm for oral gel compositions, and from about 50 ppm to about 250 ppm fluoride for oral rinses.

In compositions of the present invention, preservatives may be used, especially in nonalcohol or low alcohol compositions. These include benzoic acid, sodium benzoate, methylparaben, propylparaben, sorbic acid and potassium sorbate. These preservative agents are generally present at levels ranging from about 0% by weight to about 2% by weight.

Thickening agents or binders are an optional component of the compositions and can be used if they are compatible with zinc and CPC cations. Compatible thickening agents and binders should not substantially inactivate the zinc and CPC in the composition. Examples of such thickening agents or binders include cellulose gums such as methyl cellulose, cellulose derivatives such as hydroxyethylcellulose and quaternary-compatible silicas. Thickeners are usually present in the claimed compositions from about 0% by weight to about 2% by weight in oral rinses, in which hydroxyethylcellulose gum is the preferred thickener. In oral gels, quaternary-compatible silica-based thickeners can be used at concentrations from about 0% by weight to about 20% by weight. "Sylodent" by W. R. Grace & Co. is the tradename of the preferred silica-based thickener.

Orally acceptable sweetening agents such as saccharin, lactose, maltose, aspartame, sodium cyclamate, and polydextrose can be added to the compositions. Sweetening agents generally are present in an amount ranging from about 0.001% by weight to about 5% by weight for oral rinse and oral gel compositions. Orally acceptable coloring agents generally are present in an amount ranging from about 0% by weight to about 0.01% by weight.

EXAMPLE 1

A 0.15% by weight zinc chloride, 0.1% CPC oral rinse composition was formulated by first dissolving the Poloxamer in the water at room temperature (usually about 25° C.), using a Master Servodyne mixer with high-lift blade rotating at 200–300 rpm to give a clear aqueous solution. Next, sodium citrate, citric acid, hydrochloric acid, sodium saccharin, dyes and sorbitol were added to the solution which was mixed until these ingredients dissolved. The zinc chloride and CPC were then added to the solution which was mixed until these ingredients were dissolved. The flavor was added to the 190° alcohol to give a clear alcoholic solution. The alcoholic phase was added slowly to the aqueous phase which was continually agitated until the addition was complete. The resulting blue-green product was mixed for an additional 30 minutes. The product had a pH of approximately 4.25. It was clear and uniform in appearance and did not cloud on storage at –5° C. for 7 days.

| Ingredient | Weight Percent |
| --- | --- |
| Poloxamer 407 | 0.50 |
| Sodium Citrate | 0.14 |
| Citric Acid (Anhydrous) | 0.01 |
| Hydrochloric Acid (12N) | 0.0045 |
| Sodium saccharin | 0.02 |
| FD&C Blue No. 1 | 0.00015 |
| D&C Green No. 5 | 0.00045 |
| Sorbitol Solution (70%) | 20.0 |
| Zinc Chloride | 0.15 |
| Cetyl pyridinium Chloride | 0.10 |
| Alcohol, Ethyl 190 proof | 14.00 |
| Flavor | 0.145 |
| Purified water | 64.92990 |
| Total | 100.00000 |

EXAMPLE 2

A 0.25% by weight zinc chloride, 0.1% CPC oral rinse was formulated by first dissolving the Poloxamer in the water at room temperature, using a Master Servodyne mixer with high-lift blade rotating at 200–300 rpm to give a clear aqueous solution. Next, sodium citrate, citric acid, hydrochloric acid, sodium saccharin, dyes and the sorbitol were added to the solution and mixed until they were dissolved. The zinc chloride and CPC were then added to the solution which was mixed until these ingredients were dissolved. The flavor was added to the 190° alcohol to give a clear alcoholic solution. The alcoholic phase was added slowly to the aqueous phase which was continually agitated until the addition was complete. The resulting blue-green product was mixed for a further 30 minutes. The product had a pH of approximately 3.0. It was clear and uniform in appearance and did not cloud on storage at –5° C. for 7 days.

| Ingredient | Weight Percent |
| --- | --- |
| Poloxamer 407 | 0.50 |
| Sodium Citrate | 0.20 |
| Citric Acid (Anhydrous) | 0.80 |
| Hydrochloric Acid (12N) | 0.0045 |
| Sodium saccharin | 0.02 |
| FD&C Blue No. 1 | 0.00015 |
| D&C Green No. 5 | 0.00045 |
| Sorbitol Solution (70%) | 20.0 |
| Zinc Chloride | 0.25 |
| Cetyl pyridinium Chloride | 0.10 |
| Alcohol, Ethyl 190 proof | 14.00 |
| Flavor | 0.145 |
| Purified water | 64.97990 |
| Total | 100.00000 |

EXAMPLE 3

A 0.6% by weight zinc chloride, 1.0% by weight CPC oral gel composition was formulated in several phases. The first phase consisted of first dissolving, in a Hobart mixer, the methyl cellulose and hydroxy ethyl cellulose in the polyethylene glycol (PEG-8) and glycerin. A second phase involved dissolving the NaF in water in a separate container. To the NaF solution, the following were added: citric acid, sodium citrate, and zinc chloride. For the third phase, the CPC was dissolved in water. To that CPC solution, Tego Betaine E was added. Next, phases 2 and 3 were combined. The combined phases were then added to phase 1 in the Hobart mixer. The sodium saccharin and dyes (as concentrated solutions) were added to the Hobart mixer and mixed for 5 minutes. Next, the silica was added to the Hobart mixer until a homogenous thick paste was obtained. Next, the flavor was mixed with Polysorbate 80 and then added to the gel and mixed for a minimum of 10 minutes. The gel was then deaerated in a 30 psi vacuum for at least 5 minutes. A clear blue-green gel was obtained. A 3:1 slurry of the gel had a pH of approximately 4.0–4.5.

| Ingredient | Weight Percent |
| --- | --- |
| Phase 1 | |
| Methyl Cellulose | 4.000 |
| Hydroxy Ethyl Cellulose | 3.000 |
| PEG-8 | 3.000 |
| Glycerin (99.5%) | 47.851 |
| Phase 2 | |
| Purified Water | 5.000 |
| Sodium Fluoride | 0.243 |
| Citric Acid | 0.700 |
| Sodium Citrate | 0.600 |
| Zinc Chloride | 0.600 |
| Phase 3 | |
| Cetyl pyridinium Chloride | 1.000 |
| Purified Water | 1.500 |
| TEGO Betaine E | 4.000 |
| Sodium Saccharin | 0.500 |
| D&C Yellow No. 10 | 0.001 |
| FD&C Blue No. 1 | 0.005 |
| Sylodent Silica (SMR6-26-50A), quat compatible | 25.000 |
| Polysorbate 80 | 2.000 |
| Flavor | 1.000 |
| Total | 100.000 |

We claim:
1. A stable oral rinse or clear oral gel composition, comprising:

a) about 0.01% by weight to about 1% by weight of hydrated uncomplexed zinc cations;
b) about 0.01% by weight to about 4% by weight of fully or partially protonated citrate moieties;
c) about 0.01% by weight to about 2% by weight of cetyl pyridinium moieties; and
d) an orally acceptable vehicle;
wherein said composition has a pH of from about 3.0 to about 4.5, said composition is substantially optically clear and substantially free of precipitants, flocculants, or crystals at about room temperature, said composition does not contain zinc citrate complexes selected from the group consisting of $Zn(CIT)^-$, $Zn(CIT)_2^{4-}$ and $Zn(CIT)OH^{2-}$, and the unpleasant taste and aftertaste of said zinc cations and said cetyl pyridinium moieties are masked.

2. The composition of claim 1, wherein the zinc cations are hydrated zinc cations.

3. The composition of claim 1, wherein the zinc cations are formed from zinc chloride, zinc sulfate, zinc gluconate, zinc acetate, and zinc lactate.

4. The composition of claim 1, wherein the amount of zinc cation ranges from about 0.02% by weight to about 0.25% by weight.

5. The composition of claim 1, wherein the fully or partially protonated citrate moieties are formed from citric acid, a soluble pharmaceutically acceptable citrate salt, or mixtures thereof.

6. The composition of claim 1, wherein the amount of fully or partially protonated citrated moieties ranges from about 0.02% by weight to about 1% by weight.

7. The composition of claim 1, wherein the cetyl pyridinium moieties are formed from a cetyl pyridinium pharmaceutically acceptable salt.

8. The composition of claim 1, wherein the amount of cetyl pyridinium moieties ranges from about 0.025% by weight to about 1% by weight.

9. The composition of claim 5, wherein the soluble pharmaceutically acceptable citrate salt is selected from the group consisting of sodium citrate, ammonium citrate, potassium citrate, or mixtures thereof.

10. The composition of claim 1, further including from about 0.01% by weight to about 10.0% by weight of an orally acceptable surfactant selected from the group consisting of nonionic surfactants, amphoteric surfactants, or mixtures thereof.

11. The composition of claim 10, wherein said composition is an oral rinse and including from about 0.01% by weight to about 1% by weight of said surfactant.

12. The composition of claim 10, wherein said composition is an oral gel and including from about 0.5% by weight to about 5% by weight of said surfactant.

13. The composition of claim 1, wherein said composition is an oral rinse and further including up to about 25.0% by weight of an orally acceptable alcohol.

14. The composition of claim 1, wherein said composition is an oral gel and further including up to 60% by weight of an orally acceptable dental abrasive.

15. The composition of claim 14, wherein the orally acceptable dental abrasive is selected from the group consisting of silica, alumina, β-phase calcium pyrophosphate and calcium carbonate.

16. The composition of claim 1, further including from about 50 ppm to about 500 ppm fluoride.

17. The composition of claim 16, wherein the composition in an oral rinse and the amount of fluoride is from about 50 ppm to about 250 ppm.

18. The composition of claim 16, wherein the composition is an oral gel and the amount of fluoride is from about 250 ppm to about 1500 ppm.

19. A stable oral rinse composition, comprising:
a) about 0.01% by weight to about 1% by weight of hydrated uncomplexed zinc cations;
b) about 0.01% by weight to about 2% by weight of fully or partially protonated citrate moieties, wherein the citrate moieties are formed from citric acid, a soluble pharmaceutically acceptable citrate salt, or mixtures thereof;
c) about 0.01% by weight to about 1% by weight of cetyl pyridinium moieties;
d) about 0.01% by weight to about 1% by weight of an orally acceptable surfactant selected from the group consisting of nonionic surfactants, amphoteric surfactants, or mixtures thereof;
e) from 0 to about 25.0% by weight of an orally acceptable alcohol;
f) about 50 ppm to about 250 ppm of fluoride; and
g) an orally acceptable vehicle;
wherein said composition has a pH of from about 3.0 to about 4.5, said composition is substantially optically clear and substantially free of precipitants, flocculants, or crystals at about room temperature, said composition does not contain zinc citrate complexes selected from the group consisting of $Zn(CIT)^-$, $Zn(CIT)_2^{4-}$ and $Zn(CIT)OH^{2-}$, and the unpleasant taste and aftertaste of said zinc cations and said cetyl pyridinium moieties are masked.

20. The composition of claim 19, wherein the zinc cations are hydrated zinc cations.

21. The composition of claim 19, wherein the amount of zinc cation ranges from about 0.02% by weight to about 0.25% by weight.

22. The composition of claim 19, wherein the cetyl pyridinium moieties are formed from a cetyl pyridinium pharmaceutically acceptable salt.

23. The composition of claim 19, wherein the amount of cetyl pyridinium moieties ranges from about 0.025% by weight to about 1 % by weight.

24. The composition of claim 19, wherein the soluble pharmaceutically acceptable citrate salt is selected from the group consisting of sodium citrate, ammonium citrate, potassium citrate, or mixtures thereof.

25. The composition of claim 19, wherein the amount of fully or partially protonated citrated moieties ranges from about 0.02% by weight to about 1 % by weight.

26. A clear oral gel composition, comprising:
a) about 0.01% by weight to about 1% by weight of hydrated uncomplexed zinc cations;
b) about 0.01% by weight to about 4% by weight of fully or partially protonated citrate moieties wherein the citrate moieties are formed from citric acid, a soluble pharmaceutically acceptable citrate salt, or mixtures thereof;
c) about 0.01% by weight to about 2% by weight of cetyl pyridinium moieties;
d) about 0.5 to about 5% by weight of an orally acceptable surfactant selected from the group consisting of nonionic surfactants, amphoteric surfactants, or mixtures thereof;
e) from 0 to 60% by weight of an orally acceptable dental abrasive;
f) about 250 ppm to about 1500 ppm of fluoride; and g) an orally acceptable vehicle;
wherein said composition has a pH of from about 3.0 to about 4.5, said composition is substantially optically clear and substantially free of precipitants, flocculants, or crystals at about room temperature, said composition does not contain zinc citrate complexes selected from the group consisting of $Zn(CIT)^-$, $Zn(CIT)_2^{4-}$ and $Zn(CIT)OH^{2-}$, and the unpleasant taste and aftertaste of said zinc cations and said cetyl pyridinium moieties are masked.

27. The composition of claim 25, wherein the zinc cations are hydrated zinc cations.

28. The composition of claim 25, wherein the amount of zinc cation ranges from about 0.02% by weight to about 0.25% by weight.

29. The composition of claim 26, wherein the cetyl pyridinium moieties are formed from a cetyl pyridinium pharmaceutically acceptable salt.

30. The composition of claim 25, wherein the amount of cetyl pyridinium moieties ranges from about 0.025% by weight to about 1% by weight.

31. The composition of claim 26, wherein the soluble pharmaceutically acceptable citrate salt is selected from the group consisting of sodium citrate, ammonium citrate, potassium citrate, or mixtures thereof.

32. The composition of claim 25, wherein the amount of fully or partially protonated citrated moieties ranges from about 0.02% by weight to about 1% by weight.

33. The composition of claim 26, wherein the orally acceptable dental abrasive is selected from the group consisting of silica, alumina, β-phase calcium pyrophosphate and calcium carbonate.

* * * * *

UNITED STATES PATENT AND TRADEMARK OFFICE
CERTIFICATE OF CORRECTION

PATENT NO : 5,948,390

DATED : September 7, 1999

INVENTOR(S) : Dennis G.A. Nelson and Alejandro V. Ortega II

It is certified that error appears in the above-identified patent and that said Letters Patent are hereby corrected as shown below:

On the left hand column of the cover page, the correct spelling of one of the inventors is "Alejandro V. Ortega II."

Signed and Sealed this

Fifteenth Day of May, 2001

Attest:

NICHOLAS P. GODICI

Attesting Officer

Acting Director of the United States Patent and Trademark Office